United States Patent [19]

Kaminsky

[11] 3,966,716

[45] June 29, 1976

[54] 2H-1,3,2-DIOXABORINO-[5,4-c]-1,2-BENZO-THIAZINE 6,6-DIOXIDES

[75] Inventor: Daniel Kaminsky, Parsippany, N.J.

[73] Assignee: Warner-Lambert Company, Morris Plains, N.J.

[22] Filed: Mar. 17, 1975

[21] Appl. No.: 558,866

Related U.S. Application Data

[62] Division of Ser. No. 365,398, May 29, 1973, Pat. No. 3,898,218.

[52] U.S. Cl. .............................. 260/243 R; 424/249
[51] Int. Cl.² ....................................... C07D 279/02
[58] Field of Search ................................ 260/243 R

[56] References Cited
UNITED STATES PATENTS
3,898,218   8/1975   Kaminsky ........................ 260/243

Primary Examiner—John M. Ford
Attorney, Agent, or Firm—Albert H. Graddis; Frank S. Chow; Anne M. Kelly

[57] ABSTRACT

Process for the production of substituted pyrano[3,2-c][1,2]benzothiazine 6,6-dioxides and novel intermediates produced thereby of the general formula I:

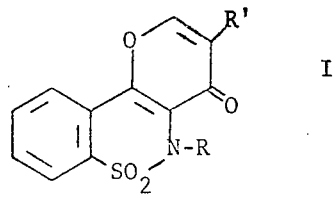

wherein R represents hydrogen and lower alkyl; R' represents lower alkyl and formyl; by reacting, as the first step, the corresponding 2-substituted-2H-1,2-benzothiazin-4(3H)-one 1,1-dioxide (II) with a boron trifluoride compound and an acid anhydride IV; alternately, the starting material may be a 3-acetyl-2-substituted-2H-1,2-benzothiazin-4-[3H]-one 1,1-dioxide (III) which is reacted with the boron trifluoride compound, without the necessity for the acid anhydride (IV). Starting materials II and III subjected to step one of the process yield novel boron complex intermediates V (2,2-difluoro-4,5-disubstituted-2H-1,3,2-dioxaborino[5,4-c]-1,2-benzothiazine 6,6-dioxide). Boron complex intermediate V, in the second step of the process, is subjected to treatment with a Vilsmeier reagent (phosphorus oxychloride together with dimethylformamide), followed by hydrolysis. The substituted-pyrano[3,2-c][1,2]benzothiazine 6,6-dioxides of formula I prepared by the process of this invention have anti-secretory activity and are useful in the treatment of hyperacidity; certain of these compounds demonstrates anti-allergy activity.

7 Claims, No Drawings

2H-1,3,2-DIOXABORINO-[5,4-c]-1,2-BENZO-THIAZINE 6,6-DIOXIDES

This is a division of application Ser. No. 365,398 filed May 29, 1973, now U.S. Pat. No. 3,898,218.

SUMMARY OF THE INVENTION

This invention relates to a novel process for preparing compounds of the formula I:

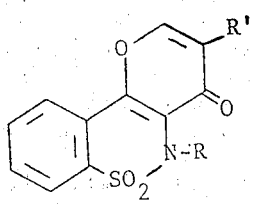

wherein R represents hydrogen and lower alkyl; R' represents lower alkyl and formyl which comprises reacting a starting material of the formula II or III:

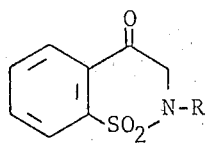 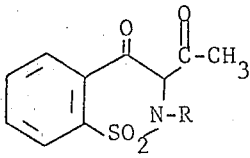

wherein R represents hydrogen and lower alkyl, with a boron trifluoride compound (preferably boron trifluoride etherate) and, in the case of starting material II, with an acid anhydride of the formula IV:

wherein R' represents hydrogen or lower alkyl, to obtain a boron complex intermediate having the formula V:

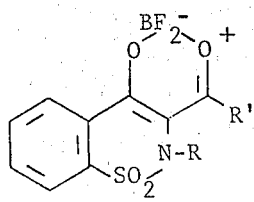

wherein R represents hydrogen, lower alkyl and lower acyl and R' represents lower alkyl; and treating intermediate V with a Vilsmeier reagent, (phosphorus oxychloride together with dimethylformamide), followed by hydrolysis. Novel intermediate compounds of the invention having formula V are useful in the preparation of final compounds having the formula I, which in turn, have therapeutic activity.

DETAILED DESCRIPTION OF THE INVENTION

Starting material II (2-substituted-2H-1,2-benzothiazin-4(3H)-one 1,1-dioxide) is reacted with an acid anhydride IV and a boron trifluoride compound in the first step of the process of this invention; alternately, starting material III (3-acetyl-2-substituted-2H-1,2-benzothiazin-4(3H)-one 1,1-dioxide) may be reacted with the boron trifluoride compound alone, the acid anhydride IV being unnecessary when starting material III is used. Using either starting material II or III in first step of the process of this invention yields the novel, substituted boron complex intermediates V which are reacted with a Vilsmeier reagent, followed by hydrolysis, to obtain the final compounds having formula I.

The Vilsmeier reagent used is phosphorus oxychloride ($POCl_3$) with dimethylformamide (DMF). The substituents obtained on final compound I depend on the boron intermediate V used. For example, if R' in the boron intermediate V is methyl (i.e., the substituent in the 4-position is methyl) and DMF is used, a final compound I is obtained wherein R' is 3-formyl, as in Examples VII to X.

However, when R' in the boron intermediate V is ethyl and DMF is used, a final compound I is obtained wherein R' is 3-methyl, as in Example XI.

Another unusual result occurs during the process of this invention when 3-acetyl-2H-1,2-benzothiazin-4(3H)-one 1,1-dioxide is used as the starting material III in the process of this invention: an acetyl group attaches to the nitrogen atom of the boron intermediate complex, i.e., 5-acetyl-2,2-difluoro-4-methyl-2H-1,3,2-dioxaborino[5,4-c]1,2-benzothiazine 6,6-dioxide is formed (see Example IV). During the second step of the reaction, this 5-acetyl group is removed and the nitrogen atom in the final compound is unsubstituted.

The starting materials II and III used in the process of this invention are prepared by known methods or obvious adaptations thereof, as described in Zinnes, H. et al., 1,2-*Benzothiazines. II. The Preparation and Sodium Borohydride Reduction of 3-Acyl-2H-1,2-benzothiazin-4(3H)-one 1,1-Dioxides*, J. Org. Chem 30: 2241–2246 (1965) and in Zinnes, H. et al., 1,2-*Benzothiazines. III. The Preparation of 2H-1,2-Benzothiazin-4(3H)-one 1,1-Dioxide by the Acid-Catalyzed Deacetylation of β-Diketone*, J. Org. Chem. 31: 162–165 (1966).

The boron trifluoride compound used in the process of this invention is preferably boron trifluoride etherate.

The intermediate boron complex V prepared in the process of this invention is novel and useful in the preparation of final compounds I which are, in turn, pharmacologically active.

Novel intermediates having formula V above form an especially preferred group when R represents methyl, ethyl, butyl or acetyl; and R' represents methyl or ethyl.

Final compounds prepared according to the process of this invention, as well as certain other closely related compounds having the formula VI below:

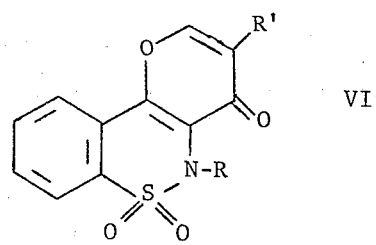

wherein R represents hydrogen and lower alkyl; and R' represents lower alkyl, formyl and hydroxymethyl and their corresponding aldehyde thiosemicarbazone derivatives, are more fully described in co-pending application U.S. Ser. NO. 365,399, filed filed May 29, 1973, now U.S. Pat. No. 3,855,216. These compounds having formula VI exhibit anti-secretory effects and can be used in relieving gastric hyperacidity. Compounds having formula VI, when administered to mammals, such as rats and guinea pigs, in a suitable vehicle as described below, inhibit the gastric secretion of hydrochloric acid; acidity in the stomach is thus reduced. Pharmaceutical compositions containing compounds of formula VI are indicated in the management of gastric hyperacidity and in the treatment of peptic ulcer resulting from such hyperacidity.

Compounds of formula VI, when tested according to the procedure of H. Shay, Gastroenterology 5: p. 43 (1945) are effective in reducing gastric acidity in the pylorus ligated rat when administered intraperitoneally at a dosage of 5 to 20 mg/kg of body weight. At a dosage of 5 to 40 mg/kg of body weight, administered intraduodenally, the same compounds are effective in reducing gastric acidity when subjected to this last mentioned test. Thus, the effective dose range for treatment of gastric hyperacidity is from 5 to 40 mg/kg of body weight of the mammal being treated, administered parenterally. Pharmaceutical compositions containing compounds having formula VI may be administered in an aqueous gum tragacanth suspension as an intramuscular injection. The dosage regimen of from 5 to 40 mg/kg of body weight may be varied depending upon the severity of the condition and the weight, age and sex of the mammal being treated.

Compounds described in aforementioned co-pending application U.S. Ser. No. 365,399, filed May 29, 1973, now U.S. Pat. No. 3,855,216, having formula VII below:

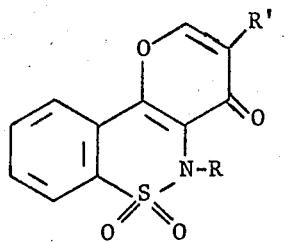

wherein R represents lower alkyl; and R' represents formyl and hydroxymethyl have also been found to be useful in the treatment of allergic conditions. Thus, compounds of formula VII reduce responses to antigen challenge by inhibiting antibody and antigen reactions in mammals when tested in accordance with the procedure of I. Mota, Life Sciences 2: No. 7, p 465–474 (1963) and Ovary, Z. et al, Proc. Soc. Exptl. Biol. Med. 81: p 584–586 (1952). The compounds may be administered to mammals such as rats or guinea pigs, parenterally or orally, at dosages of approximately 100 mg/kg of body weight.

Compounds of formula VII may be administered in a parenterally acceptable vehicle such as a gum tragacanth suspension or they may be combined with pharmaceutical diluents such as lactose, cornstarch and the like and formulated into tablet or capsule dosage forms.

Pharmaceutical compositions containing compounds of formula VII are useful in the management of allergic conditions such as bronchial asthma. To treat bronchial asthma, a dose of 100 mg/kg of body weight administered orally or parenterally is suggested. This dosage may be varied depending on the conditions of the patient.

In formulas I – VII above, the terms used to describe substituents are more fully defined as follows: "lower alkyl" is meant to include lower aliphatic hydrocarbons having 1 to 6 (preferably 1 to 4) carbon atoms in the carbon chain, such as methyl, ethyl, propyl, isopropyl, butyl, and isobutyl. The acyl in the term "lower acyl" is meant to include lower alkyl carboxylic acid wherein the "lower alkyl" moiety has the above described meaning.

In order to further illustrate the practice of this invention, the following examples are included:

EXAMPLE I

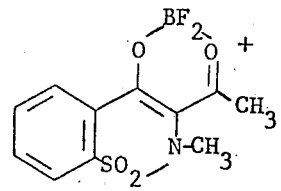

Preparation of
2,2-difluoro-4,5-dimethyl-2H-1,3,2-dioxaborino-[5,4-c]-1,2-benzothiazine 6,6-Dioxide (Procedure A)

Seventy-one grams (0.5 mole) of boron trifluoride etherate is added to 42.3 g. (0.2 mole) of 2-methyl-2H-1,2-benzothiazin-4(3H)-one 1,1-dioxide* in 102 g. (1.0 mole) of acetic anhydride. The mixture is heated for 4 hrs. on a steam bath and then refluxed for 1 hr. The mixture is cooled, diluted with 250 ml. of ether, stirred and filtered to yield It. brown solid complex; mp 163°–172°C. [Dry weight = 58.7 g. (97%)]. The analytical sample is obtained by recrystallization from ethyl acetate: Skellysolve C; mp 213°–214°C.

*Prepared by the method of H. Zinnes, R. A. Comes and J. Shavel, Jr., J. Org. Chem., 31, 162 (1966).

Anal. Calcd for $C_{11}H_{10}BF_2NO_4S$: C, 43.88; H, 3.35; H, 4.65; S, 10.65. Found: C, 44.16; H, 3.43; N, 4.55; S, 10.75.

EXAMPLE II

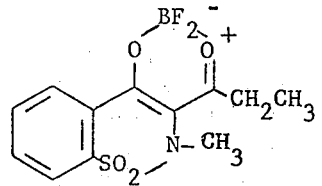

Preparation of
4-ethyl-2,2-difluoro-5-methyl-2H-1,3,2-dioxaborino-[5,4-c]1,2-benzothiazine 6,6-Dioxide (Procedure A)

Starting with 2-methyl-2H-1,2-benzothiazin-4(3H)-one 1,1-dioxide* and following the procedure A of Example I, but substituting propionic anhydride for acetic anhydride, 4-ethyl-2,2-difluoro-5-methyl-2H-1,3,2-dioxaborino[5,4-c]1,2-benzothiazine 6,6-dioxide is obtained having an mp of 134°–136°C.

*Prepared by the method of H. Zinnes, R. A. Comes and J. Shavel, Jr., J. Org. Chem., 31, 162 (1966).

Anal. Calcd: $C_{12}H_{12}BF_2NO_4S$: C, 45.74; H, 3.84; N, 4.45; F, 12.06. Found: C, 45.62; H, 3.94; N, 4.19; F, 12.17.

EXAMPLE III

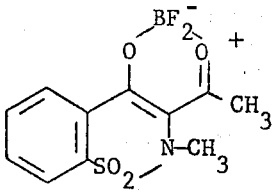

Preparation of 2,2-difluoro-4,5-dimethyl-2H-1,3,2-dioxaborino-[5,4-c]-1,2-benzothiazine 6,6-Dioxide (Procedure B)

Boron trifluoride etherate (142 g., 1.0 mole) is added to a mixture of 101 g. (0.4 mole) of 3-acetyl-2-methyl-2H-1,2-benzothiazin-4(3H)-one 1,1-dioxide* and 100 ml. of $Ac_2O$. This mixture is heated on a steam bath (permitting volatiles to escape) for 2 hours, then refluxed for 1 hr. After standing overnight, the mixture is diluted with about 500 ml $Et_2O$, cooled, scratched and filtered. The crude lt. brown crystals are washed several times with ether and dried to yield 76.5% of material melting at 174°–183°C. The analytical sample from EtOAc: Skelly C melted at 213°–214°C. and is identical to the material prepared by Example I.

*Prepared by method of H. Zinnes, R. A. Comes, F. R. Zuleski, A. N. Caro and J. Shavel, Jr., J. Org. Chem., 30, 2241 (1965).

EXAMPLE IV

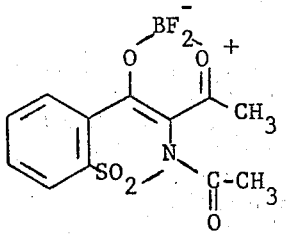

Preparation of 5-acetyl-2,2-difluoro-4-methyl-2H-1,3,2-dioxaborino-[5,4-c]1,2-benzothiazine 6,6-Dioxide (Procedure B)

Starting with 3-acetyl-2H-1,2-benzothiazin-4(3H)-one 1,1-dioxide* and following procedure B of Example III, 5-acetyl-2,2-difluoro-4-methyl-2H-1,3,2-dioxaborino[5,4-c]1,2-benzothiazine 6,6-Dioxide is obtained having an mp of 195°–197°C.

*Prepared by the method of H. Zinnes, R. A. Comes and J. Shavel, Jr., J. Org. Chem., 31: 162 (1966)

Anal. Calcd: $C_{12}H_{10}BF_2NO_5S$: C, 43.80; H, 3.06; S, 9.74. Found: C, 44.13; H, 3,08; S, 9.85.

EXAMPLE V

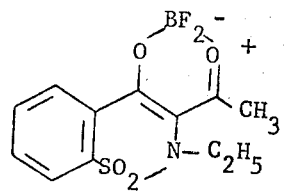

Preparation of 5-ethyl-2,2-difluoro-4-methyl-2H-1,3,2-dioxaborino-[5,4-c]1,2-benzothiazine 6,6-Dioxide (Procedure B)

Starting with 3-acetyl-2-ethyl-2H-1,2-benzothiazin-4(3H)-one 1,1-dioxide and following the procedure B of Example III, 5-ethyl-2,2-difluoro-4-methyl-2H-1,3,2-dioxaborino[5,4-c]1,2-benzothiazine 6,6-Dioxide is obtained having an mp of 167°–169°C.

Anal. Calcd.: $C_{12}H_{12}BF_2NO_4S$: C, 45.74; H, 3.84; S, 10.18. Found: C, 45.50; H, 3.87; S, 10.39.

EXAMPLE VI

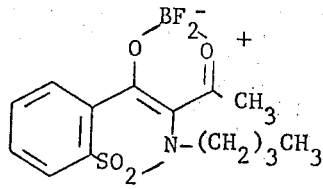

Preparation of 5-n-butyl-4-methyl-2H-1,3,2-dioxaborino[5,4-c]1,2-benzothiazine 6,6-Dioxide (Procedure B)

Starting with 3-acetyl-2-n-butyl-2H-1,2-benzothiazin-4(3H)-one 1,1-dioxide and following the procedure B of Example III, 5-n-butyl-4-methyl-2H-1,3,2-dioxaborino[5,4-c]1,2-benzothiazine 6,6-dioxide is obtained having an mp of 100°–102°C.

Anal. Calcd: $C_{14}H_{16}BF_2NO_4S$: C, 49.00; H, 4.73; S, 9.34. Found: C, 49.16; H, 4.73; S, 9.41.

EXAMPLE VII

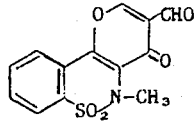

Preparation of 5-methyl-4-oxo-4H,5H-pyrano[3,2-c][1,2]benzothiazine-3-carboxaldehyde 6,6-Dioxide (Procedure C)

A solution of reagent is prepared by the slow addition of 153 g. (1.0 mole) of phosphorus oxychloride to ice cold DMF (365 g., 5 moles). The temperature is maintained below 10°C by use of a cooling bath. After stirring for an additional half-hour, 150 g. (0.5 mole) of 2,2-difluoro-4,5-dimethyl-2H-1,3,2-dioxaborino[5,4-c]-1,2-benzothiazine 6,6-dioxide is added and the reaction mixture is stirred for 15 minutes. The mixture is heated for 2 hours on a steam bath and poured over 2500 ml. ice water. After standing overnight, the mixture is filtered to yield lt. brown solid product; mp 246°–254°C. Dry weight equals 131.6 g. (90% yield). The analytical material, recrystallized from DMF, melted at 258°–259°C (dec).

Anal. Calcd for $C_{13}H_9NO_5S$: C, 53.61; H, 3.11; N, 4.81; S, 11.01. Found: C, 53.33; H, 309; N, 4.90; S, 10.83.

EXAMPLE VIII

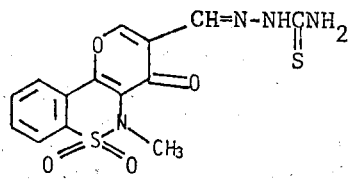

Preparation of 5-methyl-4-oxo-4H,5H-pyrano[3,2-c]-1,2-benzothiazine-3-carboxaldehyde 3-thiosemicarbazone 6,6-dioxide hemihydrate The product of Example VII is reacted with thiosemicarbaside in dioxane to obtain 5-methyl-4-oxo-4H,5H-pyrano[3,2-c]-1,2-benzothiazine-3-carboxaldehyde 3-thiosemicarbazone 6,6-dioxide hemihydrate having an mp of 227°–229°C (dec).

Anal. Calcd: $C_{14}H_{12}N_4S_2O_{4.1/2}H_2O$: C, 45.03; H, 3.51; N, 15.00; S, 17.17. Found: C, 45.13; H, 3,49; N, 14.91; S, 16.85.

EXAMPLE IX

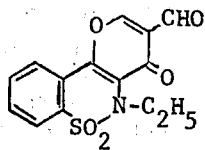

Preparation of 5-ethyl-4-oxo-4H,5H-pyrano[3,2-c][1,2]benzo-thiazine-3-carboxaldehyde 6,6-dioxide (Procedure C)

Starting with 5-ethyl-2,2-difluoro-4-methyl-2H-1,3,2-dioxaborino[5,4-c]1,2-benzothiazine 6,6-dioxide from Example V and following procedure C of Example VII, 5-ethyl-4-oxo-4H,5H-pyrano[3,2-c][1,2]benzothiazine-3-carboxaldehyde 6,6-dioxide is obtained having an mp of 160°–162°C.

Anal. Calcd: $C_{14}H_{11}NO_5S$: C, 55.08; H, 3.63; N, 4.59. Found: C, 54.96; H, 3.56; N, 4.11.

EXAMPLE X

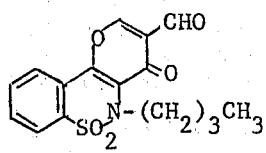

Preparation of 5-n-butyl-4-oxo-4H,5H-pyrano[3,2-c][1,2]benzo-thiazine-3-carboxaldehyde 6,6 1dioxide (Procedure C)

Starting with 5-n-butyl-4-methyl-2H-1,3,2-dioxaborino[5,4-c] 1,2-benzothiazine 6,6-dioxide from Example VI, and following procedure C of Example VII 5-n-butyl-4-oxo-4H,5H-pyrano[3,2-c] [1,2]benzothiazine-3-carboxaldehyde 6,6-dioxide is obtained, having an mp of 108°–110°C.

Anal. Calcd.: $C_{16}H_{15}NO_5S$: C, 57.65; H, 4.54; N, 4.20. Found: C, 57.70; H, 4.58; N, 4.24.

EXAMPLE XI

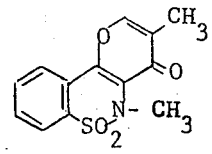

Preparation of 3,5-Dimethylpyrano[3,2-c][1,2]benzothiazin-4(5H)-one 6,6-dioxide (Procedure C)

Starting with 4-ethyl-2,2-difluoro-5-methyl-2H-1,3,2-dioxaborino[5,4-c]-1,2-benzothiazine 6,6-dioxide from Example II and using procedure C of Example VII, the subject compound is obtained as an almost colorless crystalline product; mp 214°–216°C (from chloroform: Skellysolve C).

Anal. Calcd: $C_{13}H_{11}NO_4S$: C, 56.31; H, 4.00; N, 5.05. Found: C, 56.20; H, 3.97; N, 5.07.

What is claimed is:

1. A compound of the formula II:

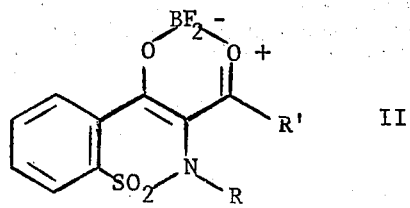

wherein R represents hydrogen, lower alkyl and lower alkanoyl; R' represents lower alkyl.

2. A compound according to claim 1 wherein R represents methyl, ehtyl, butyl, and acetyl; and wherein R' represents methyl and ethyl.

3. A compound according to claim 1 which is 2,2-difluoro-4,5-dimethyl-2H-1,3,2-dioxaborino[5,4-c]-1,2-benzothiazine 6,6-dioxide.

4. A compound according to claim 1 which is 4-ethyl-2,2-difluoro-5-methyl-2H-1,3,2-dioxaborino[5,4-c]1,2-benzothiazine 6,6-dioxide.

5. A compound according to claim 1 which is 5-acetyl-2,2-difluoro-4-methyl-2H-1,3,2-dioxaborino[5,4-c]1,2-benzothiazine 6,6-dioxide.

6. A compound according to claim 1 which is 5-ethyl-2,2-difluoro-4-methyl-2H-1,3,2-dioxaborino[5,4-c]1,2-benzothiazine 6,6-dioxide.

7. A compound according to claim 1 which is 5-n-butyl-4-methyl-2H-1,3,2-dioxaborino[5,4-c]1,2-benzothiazine 6,6-dioxide.

* * * * *